United States Patent [19]

Shevade et al.

[11] Patent Number: 5,855,877
[45] Date of Patent: Jan. 5, 1999

[54] NON-AQUEOUS ANTIPERSPIRANT COMPOSITION

[75] Inventors: Makarand Shevade, Plainsboro; Robert Bianchini, Belle Mead; Francis J. Bala, Jr., Sayreville, all of N.J.

[73] Assignee: Colgate-Palmolive Company, New York, N.Y.

[21] Appl. No.: 709,445

[22] Filed: Sep. 6, 1996

[51] Int. Cl.⁶ .................................. A61K 7/32; A61K 7/00
[52] U.S. Cl. ............................. 424/65; 424/66; 424/67; 424/68; 424/400; 424/401
[58] Field of Search .................... 424/65, 66, 67, 424/68, 400, 401

[56] References Cited

U.S. PATENT DOCUMENTS

| | | |
|---|---|---|
| 4,526,780 | 7/1985 | Marschner et al. . |
| 4,605,018 | 8/1986 | de la Guardia et al. . |
| 4,919,934 | 4/1990 | Deckner et al. . |
| 4,937,069 | 6/1990 | Shin . |
| 5,019,375 | 5/1991 | Tanner et al. . |
| 5,069,897 | 12/1991 | Orr . |
| 5,102,656 | 4/1992 | Kasat . |
| 5,156,834 | 10/1992 | Beckmeyer et al. . |
| 5,244,665 | 9/1993 | Natraj et al. ............................. 424/401 |
| 5,292,530 | 3/1994 | McCrea et al. ........................... 424/66 |
| 5,429,816 | 7/1995 | Hofrichter et al. . |
| 5,444,096 | 8/1995 | McCrea et al. ......................... 514/770 |
| 5,470,861 | 11/1995 | Harmon . |
| 5,478,555 | 12/1995 | Bara et al. . |
| 5,531,986 | 7/1996 | Shevade et al. ........................... 424/68 |

FOREIGN PATENT DOCUMENTS

| | | |
|---|---|---|
| 0028853 | 10/1980 | European Pat. Off. . |
| 0135315B2 | 7/1984 | European Pat. Off. . |
| 0281288B1 | 2/1988 | European Pat. Off. . |
| 0295071 | 6/1988 | European Pat. Off. . |
| 0307605 | 8/1988 | European Pat. Off. . |
| 0330140 | 2/1989 | European Pat. Off. . |
| 0343843B1 | 5/1989 | European Pat. Off. . |
| 0377209 | 12/1989 | European Pat. Off. . |
| 0388111B1 | 3/1990 | European Pat. Off. . |
| 0396137 | 5/1990 | European Pat. Off. . |
| 0400546B1 | 5/1990 | European Pat. Off. . |
| 0485012A1 | 10/1991 | European Pat. Off. . |
| 0665007 | 8/1995 | European Pat. Off. . |
| 9603962 | 2/1996 | European Pat. Off. . |
| 2221805 | 2/1996 | United Kingdom . |
| 2299024 | 9/1996 | United Kingdom . |
| WO91/04009 | 4/1991 | WIPO . |
| WO94/24993 | 11/1994 | WIPO . |

*Primary Examiner*—Shelley A. Dodson
*Attorney, Agent, or Firm*—William I. Solomon; Rosemary M. Miano

[57] ABSTRACT

Disclosed is a non-aqueous composition for reducing body malodor, containing an antiperspirant active material, volatile silicone material, non-volatile emollient material (e.g., non-volatile silicone emollient material), and a thickening agent, the thickening agent including a gelling agent which is a solid plasticizer. Illustrative gelling agents are hydroxy polyester and polydimethylsiloxanyl beeswax. Other beeswax derivatives whose free fatty acids have been reacted with silicone materials can also be used as the gelling agent for compositions of the present invention. The compositions of the present invention can be formulated as antiperspirant creams by incorporating appropriate amounts of antiperspirant active material and thickening agent in the composition, and can be used to reduce axillary perspiration. Compositions of the present invention have good rheological and viscoelastic properties.

41 Claims, 5 Drawing Sheets

NON-AQUEOUS ANTIPERSPIRANT COMPOSITION

BACKGROUND OF THE INVENTION

The present invention is directed to a non-aqueous composition for reducing body malodor (for example, a non-aqueous antiperspirant composition), which leaves substantially no visible (white) residue on the skin, which is stable and exhibits substantially no syneresis (fluid separation), and which has excellent rheology characteristics as, e.g., a cream composition, while maintaining a soft skin feel. In particular, the present invention is directed to a non-aqueous solid (for example, cream) antiperspirant composition containing at least one antiperspirant active material suspended in the composition, the composition being stable and homogeneous, and leaving substantially no visible residue on the skin.

Antiperspirant products are well known in the art. Antiperspirant products have appeared in the market in various dosage forms, such as sticks, gels, roll-ons, aerosols and creams. Of these dosage forms, for example, various sticks, gels and creams are constituted by a liquid base material solidified by a solidifying agent, and these fall within solid compositions according to the present invention. Generally, the dosage forms include a solution of the active ingredient in a suitable solvent, a suspension of the active ingredient in a non-solvent, or a multiphasic dispersion or emulsion in which a solution of the active ingredient is dispersed in some continuous phase or in which the solubilized active ingredient constitutes the continuous phase.

A variety of cream formulations (also known as soft solids or semi-solids) are known. Various of these cream formulations include a clay thickening agent, and an activator for such clay thickening agent. See, for example, U.S. Pat. No. 5,019,375 to Tanner, et al., and U.S. Pat. No. 4,526,780 to Marschner, et al., the contents of each of which are incorporated herein by reference in their entirety.

Other cream compositions contain a particulate thickening agent such as fumed silica. See U.S. Pat. No. 5,069,897 to Orr and U.S. Pat. No. 4,937,069 to Shin.

This U.S. Pat. No. 4,937,069 to Shin discloses a substantially anhydrous antiperspirant semi-solid composition, containing specific amounts of an antiperspirant active powder, thickening/suspending agents containing fumed silica, thickening/solid emollients, non-volatile liquid emollients/plasticizers, and volatile emollients. This patent discloses that the non-volatile liquid emollients/plasticizers are utilized in order to avoid a product which produces a waxy grainy powder on the skin after the volatile emollients evaporate, the addition of the non-volatile liquid emollients/plasticizers leaving a fine, creamy, silky residue on the skin and also imparting good adherence to the skin. The contents of U.S. Pat. No. 4,937,069 to Shin are incorporated herein by reference in their entirety.

U.S. Pat. No. 5,102,656 to Kasat, the contents of which are incorporated herein by reference in their entirety, discloses a creamy, heterogeneous and anhydrous antiperspirant product containing, in percent by weight of the total weight of the composition, 30–70% of a volatile silicone product as a carrier, 7–30% of a suitable gelling agent or agents, and about 12–30% of a physiologically acceptable antiperspirant agent. This patent discloses that the gelling agent can be any of a number of compositions, including, for example, hydrogenated vegetable oil, hydrogenated castor oil, fatty acids, beeswax, paraffin wax, fatty alcohols, polyethylene and the like.

Notwithstanding all of the foregoing, it is still desired to provide a cosmetic composition that is stable, exhibiting no syneresis (fluid separation), and is homogeneous, and which leaves substantially no residue upon application to the skin is or after drying of the applied composition, while maintaining a soft skin feel. It is also desired to provide a composition that has the foregoing properties, and is free of conventional gelling agents such as fatty alcohols and hydrogenated castor oil, while having good rheological properties. It is particularly desired to provide a non-aqueous antiperspirant cream composition, containing antiperspirant active material in particulate form suspended in the composition, the composition having the properties as discussed in the foregoing including good stability and exhibiting no visible residue while maintaining a soft skin feel, and having good rheological properties.

SUMMARY OF THE INVENTION

Accordingly, it is a first object of the present invention to provide a non-aqueous composition (for example, a non-aqueous solid composition) containing antiperspirant active materials, which leaves substantially no visible (white) residue on the skin either upon application or after drying of the composition after application, which has good cosmetic properties (including a soft skin feel), and which is stable and homogeneous (including exhibiting substantially no syneresis), and a method of making and using the same.

It is a further object of the present invention to provide such a composition, which also has good rheological properties, and a method of making and using the same.

It is a still further object of the present invention to provide such a non-aqueous composition that is easy to manufacture.

It is a still further object of the present invention to provide an antiperspirant composition (for example, an antiperspirant cream composition), which is substantially anhydrous.

The foregoing objects are achieved by the non-aqueous composition of the present invention, containing (1) an antiperspirant active material, (2) volatile silicone materials, (3) non-volatile emollient materials (e.g., non-volatile silicone emollients), and (4) a thickening agent, the thickening agent including a gelling agent which is a solid plasticizer and which acts to thicken the composition. Use of this solid plasticizer as a gelling agent, to thicken the composition, reduces crystallinity of the product (that is, reduces both the size and amount of crystals in the product), thereby increasing aesthetics of the composition (for example, providing a soft skin feel). Moreover, through use of the plasticizer which is a solid, a product having good rheological properties can be achieved.

In general, the antiperspirant active material is included in the composition in an amount sufficient to reduce malodor of the body (for example, where the composition is applied to axillary regions of the human body, the composition contains enough of the antiperspirant active material to reduce malodor arising from perspiration in the axillary regions). The thickening agent, which includes the above-described gelling agent which is a solid plasticizer, is included in the composition in an amount sufficient to provide the non-aqueous composition as a solid composition. Illustratively, the composition can include an amount of the thickening agent to provide a cream composition as the final product. Thus semi-solid or soft solid compositions fall within the scope of the present invention. Of course, where increased amounts of thickening agents are included in the composition, thicker (more viscous) solid cosmetic compositions can be provided.

The compositions according to the present invention can, desirably, also include trihydroxystearin, which is a triester of glycerin and hydroxystearic acid (trihydroxystearin is an organic derivative of castor oil).

The non-aqueous compositions according to the present invention are easy to manufacture, being formed by a mixing of the antiperspirant active material and the other components. For example, the components can be mixed at elevated temperatures, and then partially cooled (desirably prior to adding a volatile fragrance), when manufacturing the formulations of the present invention.

After the compositions according to the present invention have been formed, they can be introduced into dispensing containers as known in the art. For example, where a cream antiperspirant or deodorant composition is formed, this composition can be introduced and packaged in, e.g., conventional containers which have the appearance of a stick, but which dispense product through apertures in the top surface of the package. In use, the product is extruded onto the top surface of the package through these apertures, and the product on the top surface is rubbed, e.g., on the axillary region of the human body, so as to deposit the product containing the active antiperspirant material thereon.

Accordingly, through use of the present invention, a nonaqueous homogeneous composition (such as a deodorant or antiperspirant composition) can be provided, which leaves substantially no visible (white) residue on the skin after application and after drying of the applied film, yet which is stable (with no syneresis) while having good cosmetic properties (including maintaining a soft skin feel). Moreover, the compositions according to the present invention have good efficacy and good rheological properties.

DETAILED DESCRIPTION OF THE INVENTION

While the present invention will be described in connection with specific and preferred embodiments, it will be understood that it is not intended to limit the invention to those embodiments. To the contrary, it is intended that the present invention cover all alterations, modifications and equivalents as may be included within the spirit and scope of the invention as defined by the appended claims.

While the present invention will primarily be described in connection with antiperspirant compositions, for application to the skin, particularly to the skin in axillary regions of the human body, in order to reduce body malodor, e.g., by reducing the flow of perspiration in the axillary regions, the present invention is not limited to this specific use. Generally, the present invention is directed to compositions for reducing body malodor. By reduction of body malodor is meant that, generally, there is less body malodor after application of the composition to a person's skin (e.g., to skin in the axillary region) as compared to body malodor of the person without application of the composition. Such reduction need not necessarily be due to reduction of the flow of perspiration. The antiperspirant materials can have a deodorant function, e.g., as an antimicrobial agent. However, when the antiperspirant active materials are utilized in appropriate amounts, they primarily act to reduce malodor by reducing production of perspiration.

Throughout the present specification, where compositions are described as including or comprising specific components or materials, or methods are described as including or comprising specific processing steps, it is contemplated by the inventors that the compositions and methods of the present invention also consist essentially of, or consist of, the recited components or materials, or the recited steps. Accordingly, throughout the present disclosure any described composition of the present invention can consist essentially of, or consist of, the recited components or materials, and any method can consist essentially of, or consist of, the recited steps.

The present invention contemplates a non-aqueous composition, to reduce malodor of a human, containing an antiperspirant active material, volatile silicone materials, non-volatile emollient materials (e.g., non-volatile silicone emollient materials), and a thickening agent, the thickening agent including a gelling agent which is a solid plasticizer and which acts to thicken the composition. Through use of a solid plasticizer (e.g., which is an amorphous material), crystallinity of the product produced is reduced, while providing a product having good rheological properties. That is, through use of a gelling agent which is a plasticizer, both size of crystals in the composition, and the amount of crystals, are reduced, providing advantageous cosmetic properties. In addition, through use of a solid plasticizer, good rheological properties are achieved. By solid plasticizer, we mean plasticizers that have a melting point of at least 58° C., preferably at least 62°.

Generally, the solid plasticizers according to the present invention have a branched structure, so as to achieve the desired product characteristics including reduced crystallinity and good rheological properties, in a stable composition which leaves no visible residue.

U.S. Pat. No. 4,937,069 to Shin discloses semi-solid antiperspirant compositions containing, inter alia, non-volatile liquid emollients/plasticizers; compositions described in Shin, having the liquid emollients/plasticizers, do not achieve the advantages of the present invention, containing solid plasticizers, including, for example, the rheological properties achieved by the present invention.

Illustratively, the solid plasticizer according to the present invention can be (1) a hydroxy polyester material or (2) a derivative of beeswax in which free fatty acids of the beeswax have been reacted with silicone materials (transesterification). Thus, the derivative of beeswax, which can constitute the solid plasticizer of the composition of the present invention, can be formed by esterifying the free acid sites of the beeswax with silicone-containing materials, in order to form the silicone-containing derivative of beeswax that is the solid plasticizer.

As illustrative of these types of materials, and not limiting of the present invention, the hydroxy polyester can be $C_{18-38}$ hydroxy stearate; and the derivative of the beeswax can be polydimethylsiloxanyl beeswax.

The solid plasticizer to be incorporated in the composition of the present invention can also include PEG carnauba wax (which has a melting point in the range of 80°–85° C.).

A specific hydroxy polyester material which can be the solid plasticizer incorporated in the composition of the present invention is hydroxy stearoyl stearate. This has a melting point of 58° C.

A polydimethylsiloxanyl beeswax, which can be a solid plasticizer in the composition of the present invention, is sold by Koster Keunen, Inc. as "Siliconyl Beeswax", which is a solid amorphous material having a melting point in the range of 62°–72° C., an acid value less than 2, and a saponification value in the range of 70–90. Other chemical properties of this Siliconyl Beeswax include less than 1% free fatty acids, 11% fatty acid ester type derivatives, 15% hydrocarbons, 14% complex esters and 60% mono-esters. The Siliconyl Beeswax has the following chemical structure:

In this structure, m ranges from 22 to 30, and x is 20, giving a molecular weight for this beeswax derivative of 2500 to 2700 g/m.

Siliconyl beeswax forms non-tacky, non-greasy films on the surface of the skin, and imparts film-forming properties to emulsions and gels in which it is incorporated. It also reduces tackiness of other constituents of the composition, imparting a silky feel to the skin. Siliconyl beeswax has been used in moisturizing and facial creams.

Illustratively, and not to limit the present invention, the solid plasticizer is included in the composition in an amount of 5%–20% by weight, preferably 6%–16% by weight, of the total weight of the composition.

The volatile silicone material to be incorporated in the composition of the present invention can be those known volatile silicone materials, including cyclic and linear silicone materials. A preferred volatile silicone material is cyclomethicone. Illustratively, and not to limit the present invention, the volatile silicone material is included in the composition in an amount of 30%–70%, preferably 30%–60%, most preferably 30%–45%, by weight, of the total weight of the composition.

The non-volatile emollient material (e.g., non-volatile silicone emollient) can be any of those normally used in the art, including mixtures of at least two materials. These include, illustratively, dimethicone and PPG-14 butyl ether. Illustratively, and not to limit the present invention, the non-volatile emollient material is included in the composition in an amount of 2%–15%, preferably 5%–10%, by weight, of the total weight of the composition.

The composition of the present invention also includes an antiperspirant active material. These include, by way of example (and not of a limiting nature), aluminum chlorohydrate, aluminum chloride, aluminum sesquichlorohydrate, zirconyl hydroxychloride, aluminum-zirconium glycine complex (e.g., aluminum-zirconium tetrachlorohydrex gly), etc. The aluminum-containing materials can be commonly referred to as antiperspirant active aluminum salts. Generally, the foregoing metal-containing antiperspirant active materials are antiperspirant active metal salts. The compositions according to the present invention need not include aluminum-containing metal salts, and can include other antiperspirant active materials, including other antiperspirant active metal salts. Generally, Category I active antiperspirant ingredients listed in the Food and Drug Administration's Monograph on antiperspirant drug products for over-the-counter human use (Oct. 10, 1973) can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

The antiperspirant active material, desirably, is included as a particulate suspended in the composition of the present invention, in amounts up to, e.g., 30% by weight, of the total weight of the composition (illustratively, to reduce flow of perspiration in, e.g., axillary regions of a person, in a range of 12%–30%, preferably 14%–26%, by weight, of the total weight of the composition). This is illustrative, and is not limiting of the present invention. As an illustrative minimum amount, and not to be limiting, the composition could include at least 0.1% by weight antiperspirant active material, of the total weight of the composition; however, at low amounts (e.g., 0.1%–10% by weight, of the total weight of the composition) the material may not reduce perspiration (for example, may act as a deodorant active material, such as an antimicrobial agent, rather than to reduce perspiration). Thus, where low amounts (e.g., 0.1%–10% by weight, of the total weight of the composition) of antiperspirant active material are included in the composition, whereby the material acts as a deodorant active material, the composition can be a deodorant composition, e.g., for application to axillary regions of a person to reduce body malodor, for example, a deodorant cream composition.

Desirably, the compositions according to the present invention also include trihydroxystearin, which is a thickening agent in the composition. This material is sold, inter alia, as "Thixcin R", by Rheox, Inc. (Hightstown, N.J.). Illustratively, and not to limit the present invention, the trihydroxystearin can be included in the composition in an amount of 5%–10% by weight, preferably 5%–7% by weight, of the total weight of the composition.

The compositions according to the present invention can include other ingredients conventionally incorporated in compositions for reducing body malodor (e.g., deodorant and/or antiperspirant compositions). These include (but are not limited to), perfumes, cosmetic powders, colorants, emulsifiers, deodorant fragrances and antimicrobial agents (bacteriostats). As for various other ingredients which can be incorporated, attention is directed to the optional components such as the colorants, perfumes and fillers described in the following U.S. Patents: U.S. Pat. No. 5,019,375 to Tanner, et al. (the contents of which are incorporated herein by reference in their entirety); U.S. Pat. No. 4,937,069 to Shin (the contents of which have previously been incorporated herein by reference in their entirety); and U.S. Pat. No. 5,102,656 to Kasat (the contents of which have previously been incorporated herein by reference in their entirety).

Conventional deodorant fragrances and/or antimicrobial agents can be incorporated in compositions of the present invention. A fragrance would, illustratively, be incorporated in an amount of 0.5%–3.0% by weight, of the total weight of the composition; the antimicrobial/bacteriostat material, such as Triclosan, would preferably and illustratively be included in an amount of from 0.1% to about 0.5% by weight, of the total weight of the composition. As indicated previously, where the antiperspirant active material is included in the composition in small amounts it acts as an antimicrobial agent only and not to reduce flow of perspiration.

Illustratively, compositions according to the present invention are substantially anhydrous. Moreover, they are free of conventional gelling agents such as fatty alcohols (e.g., stearyl alcohol) and hydrogenated castor oil.

Particulate materials can also be incorporated in compositions according to the present invention, in order to further thicken the compositions. These particulate thickening materials include known clays, fumed silica, talc and other known inert materials. An illustrative particulate is Cabosil M5, from Cabot Corp.

Compositions according to the present invention can also include known inert fillers, such as (but not limited to) cornstarch, alumina, and calcium carbonate.

Compositions according to the present invention can be made by mixing the active antiperspirant material, the thickening agent (including the solid plasticizer), the volatile and non-volatile silicone materials, optionally the trihydroxystearin, and optionally other components. The mixture can be introduced into dispensing canisters, as with conventional solid compositions (e.g., conventional cream compositions). Where the solid composition is a cream (e.g., soft solid or semi-solid), these dispensing canisters can be canisters which have a top surface with slots therein, the composition being extruded onto the top surface from a reservoir in the canister, and then rubbed on the skin from the top surface so as to deposit a film of the product on the skin. See U.S. Pat. No. 5,540,361 to Fattori, issued Jul. 30, 1996, the contents of which are incorporated herein by reference in their entirety, for dispensing containers which can be used to dispense cream (semi-solid or soft solid) compositions of the present invention.

Illustratively, where the composition is an antiperspirant composition containing an antiperspirant active material for reducing perspiration in axillary regions, the composition is extruded from inside the dispensing canister through the slots onto the top surface of the dispensing canister, and from there is applied (rubbed) on the skin in the axillary regions, so as to deposit sufficient antiperspirant active material (and, if present, sufficient deodorant active material) so as to reduce perspiration and reduce body malodor originating in axillary regions of the human body.

In the following, specific examples of compositions within the scope of the present invention are set forth. Of course, these specific examples are illustrative of the present invention, and are not limiting. In these examples, the amounts of the components are in weight percent, of the total weight of the composition. In these examples, as well as throughout the present specification, various names utilized are the CTFA (Cosmetics, Toiletry and Fragrance Association, Inc.) names, as set forth in the *CFTA International Cosmetic Ingredient Dictionary* (4th Ed. 1991).

EXAMPLE 1

| Ingredient | Amount |
| --- | --- |
| Volatile silicone (cyclomethicone) | 42.00 |
| Non-volatile silicone (dimethicone) | 7.20 |
| PPG-14 Butyl Ether (Fluid AP) | 10.00 |
| Antiperspirant Active | 26.00 |
| CABOSIL M5 | 2.00 |
| THIXCIN R | 6.00 |
| Siliconyl Beeswax | 6.00 |
| Fragrance | Q.A. |

COMPARATIVE EXAMPLE 1

| Ingredient | Amount |
| --- | --- |
| Volatile silicone | 53.00 |
| Non-volatile silicone | 10.00 |
| Antiperspirant Active | 26.00 |
| CABOSIL M5 | 2.00 |
| Polyethylene | 5.00 |
| Propylene carbonate | 2.00 |
| Fragrance | Q.A. |

EXAMPLE 2

| Ingredient | Amount |
| --- | --- |
| Volatile silicone (cyclomethicone) | 38.8 |
| Non-volatile silicone (dimethicone) | 7.2 |
| PPG-14 Butyl Ether (Fluid AP) | 10.0 |
| Antiperspirant Active | 26.0 |
| CABOSIL M5 | 2.0 |
| Siliconyl Beeswax | 16.0 |
| Fragrance | Q.A. |

EXAMPLE 3

| Ingredient | Amount |
| --- | --- |
| Volatile Silicone (cyclomethicone) | 43.00 |
| Non-volatile emollient (PPG-14 Butyl Ether) | 12.00 |
| Antiperspirant Active | 26.00 |
| Siliconyl Beeswax | 16.00 |
| Hydrogenated Castor Wax | 2.00 |
| Fragrance | 1.00 |

In forming the composition of Example 1, the cyclomethicone, dimethicone, PPG-14 butyl ether (Fluid AP) and Siliconyl Beeswax were heated, along with the Cabosil M5, in a vessel at 150°–165° F., and mixed. Mixing during this process is performed using a Premier mixer.

When uniform mixing is completed, the "THIXCIN R" was added, with mixing being continued for ten more minutes. The mixture was cooled to 140° F., with fragrance then being added. The product was then filled into appropriate packages.

Corresponding processing steps were performed to provide the composition of Comparative Example 1. That is, the volatile and non-volatile silicone materials, antiperspirant active and Cabosil M5 were mixed together, the batch cooled and fragrance added.

FIGS. 1–7 show the results of rheology measurements for compositions of Examples 1 and 2, and of Comparative Example 1. Three measurements were conducted to determine rheology: a torque sweep, a frequency sweep and a shear rate sweep. These measurements can indicate resistance of a cream (soft solid or semi-solid) to stress, and can indicate if the sample exhibits stress-induced flow with recovery (viscoelasticity). The torque and frequency sweeps define viscoelastic properties of the composition, while the shear rate sweep defines viscosity properties while being sheared. These three properties are important properties for creams (soft solids or semi-solids), with respect to their flow characteristics. This is especially true for the shear rate sweep, which is a measurement made during motion of the composition.

The viscosity measurements relate to the continuous (fluid) phase of the composition. The elasticity measurements relate to how the product reacts to stress, and indicates product characteristics of recovery in the package. There needs to be a balance between the elasticity and viscosity of cream (soft solid or semi-solid) compositions, in order to achieve a composition with the most desirable properties. This balance is achieved by compositions of the present invention.

Rheology measurements shown in FIGS. 1–6, 8 and 9 were performed using a $CSL^2$ 100 Carri-Med rheometer from TA Instruments (New Castle, Del.). The following Table 1 shows the rheometer conditions and geometry used for the sweeps.

TABLE 1

Torque sweep

| | |
|---|---|
| Geometry | 4.0 cm Polyacrylic Parallel plate |
| Geometry Gap | 1000 mm |
| Initial Torque Value | 100 mN · m |
| Final Torque Value | 9000 mN · m |
| Angular Frequency | 6.283 radians/second |
| Temperature | 23° C. |
| Equilibration Time (Prior to Test) | 5 Minutes |

Frequency Sweep

| | |
|---|---|
| Geometry | 4.0 cm Polyacrylic Parallel plate |
| Geometry Gap | 1000 mm |
| Initial Angular Frequency | 0.6283 radians/second |
| Final Angular Frequency | 250 radians/second |
| Torque | 700 mN · m |
| Temperature | 23° C. |
| Equilibration Time (Prior to Test) | 5 Minutes |

Shear Rate Sweep

| | |
|---|---|
| Geometry | 4.0 cm Polyacrylic Cone, 2° Truncation |
| Geometry Gap | 57 mm |
| Initial Shear Rate | 2 1/second |
| Final Shear Rate | 25 1/second |
| Ascent/Descent Time | 1 Minute Each Direction |
| Temperature | 20° C. |
| Equilibration Time (Prior to Test) | 5 Minutes |

Figure 1:
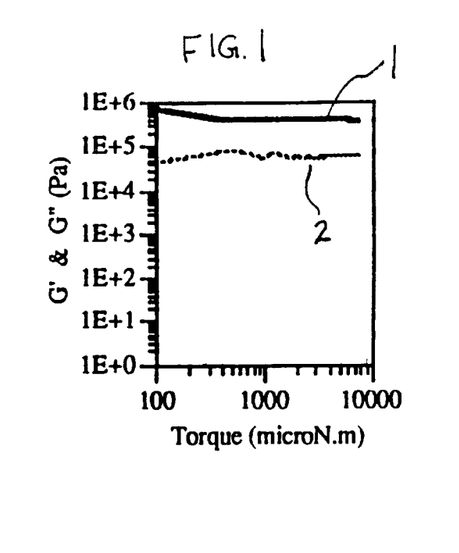
FIG. 1 is a graph showing both the storage modulus (elasticity) and loss modulus (viscosity) versus torque, for a first embodiment of the present invention.
Figure 2:
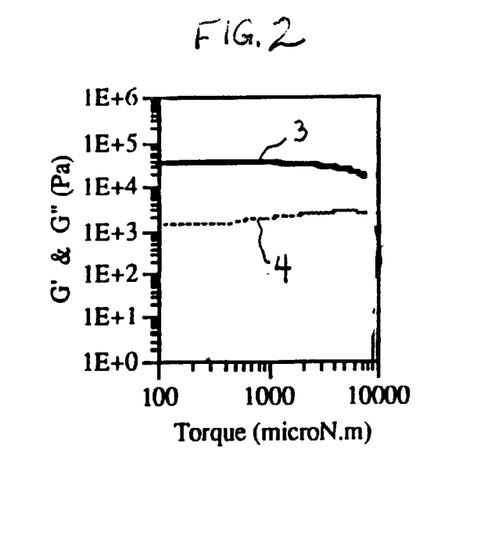
FIG. 2 is a graph showing both the storage modulus (elasticity) and loss modulus (viscosity) versus torque, for a cream formulation outside the scope of the present invention.

FIGS. 1 and 2 respectively show the torque sweeps for Example 1 and Comparative Example 1. In FIG. 1, curve 1 is the storage modulus (elasticity) and curve 2 is the loss modulus (viscosity); and in FIG. 2 curve 3 represent the storage modulus (elasticity) and curve 4 represents the loss modulus (viscosity).

As seen in FIGS. 1 and 2, the response to applied torque by the composition of Example 1 is similar to that of the composition of Comparative Example 1. The initial storage modulus (elasticity) value for Example 1 is higher than that of Comparative Example 1, with both examples resisting high levels of applied torque. Viscosity data acquired from this test at 100 mN.m indicates both samples to be very different, as shown in the following:

Example 1: 102900 Pa.S(1.9E+8cP)

Comparative Example 1: 5485 Pa.S(5.4E+6cP).

Figure 3:
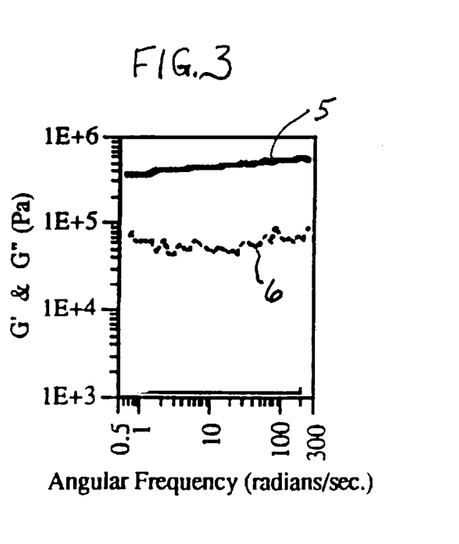
FIG. 3 is a graph showing both the storage modulus (elasticity) and loss modulus (viscosity) versus angular frequency, for this first embodiment of the present invention.
Figure 4:
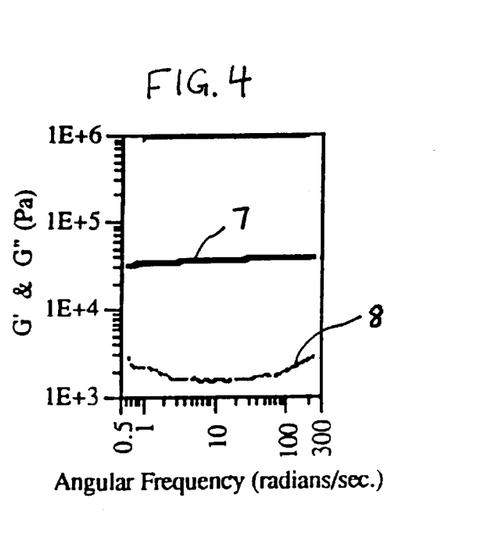
FIG. 4 is a graph showing both the storage modulus (elasticity) and loss modulus (viscosity) versus angular frequency, for a cream formulation outside the scope of the present invention.

FIGS. 3 and 4 show the frequency sweeps for the compositions respectively of Example 1 and Comparative Example 1. In FIG. 3, curves 5 and 6 respectively are the storage modulus and the loss modulus for the composition of Example 1. In FIG. 4, curves 7 and 8 respectively are the storage modulus and the loss modulus for the composition of Comparative Example 1. The difference in storage modulus, as shown by curves 5 and 7, are similar to the torque sweeps and in good agreement. Both samples have good profiles, indicating long order and short order structural integrity. In addition, the composition of Comparative Example 1 is more elastic (solid-like) than the composition of Example 1. This is derived from the tan(d) value which is the ratio of the loss modulus to storage modulus. The tan(d) at an angular frequency of 2.5 radiants/second is 0.116 for the composition of Example 1 and 0.044 for the composition of Comparative Example 1.

Figure 5:
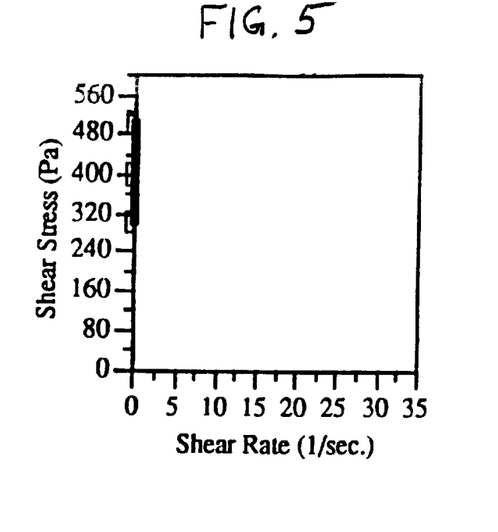
FIG. 5 is a graph showing shear stress versus shear rate, for the first embodiment of the present invention.
Figure 6:
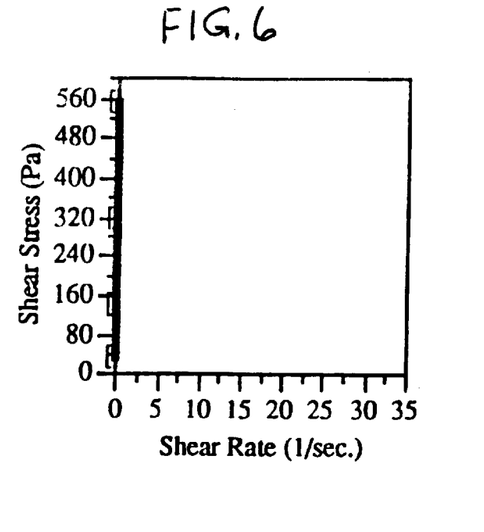
FIG. 6 is a graph showing shear stress versus shear rate, for a cream formulation outside the scope of the present invention.

Examples of thixotropic loops are shown in FIGS. 5 and 6, respectively for the composition of Example 1 and for the composition of Comparative Example 1. This test was used to simulate the shear applied by the consumer when dispensing the gel through the barrel orifices (<30 sec.$^{-1}$). It is sufficient to say that the compositions of Example 1 and Comparative Example 1 are soft solids because neither indicate flow under these conditions.

The resistance to flow is shown in the data of Table 2 below. Both samples cannot achieve any significant shear rate (flow viscosity) due to high stress.

TABLE 2

| | Shear Rate (1/s) | Shear Stress (Pa) | Viscosity (Pa · s) |
|---|---|---|---|
| Prototype I | 6.59 E-4 | 502.5 | 762,500 |
| Prototype II | 0.0145 | 550.3 | 37,950 |

Figure 7:
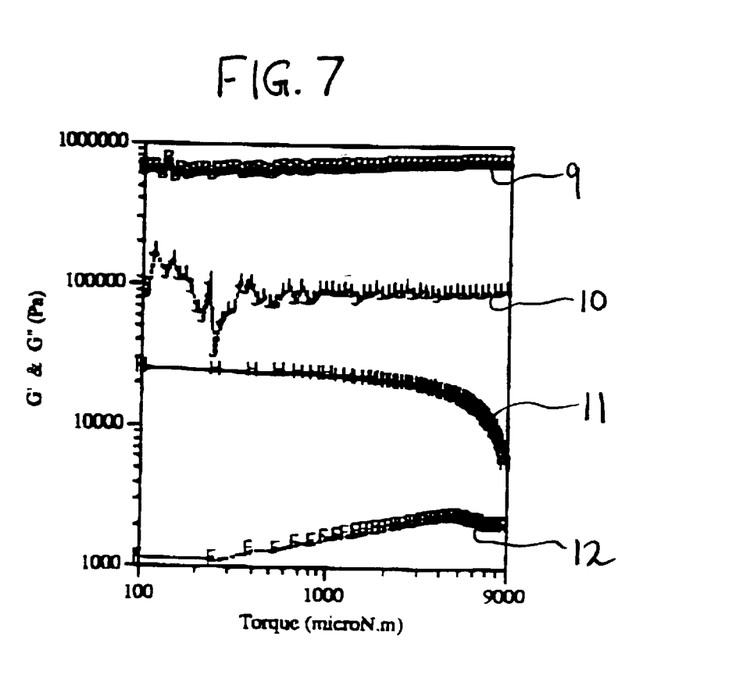
FIG. 7 is a graph showing both the storage modulus (elasticity) and loss modulus (viscosity) versus torque, for both a second embodiment of the present invention and a commercial soft solid product.

FIG. 7 shows a torque sweep comparison of the composition of Example 2, as compared to a commercial soft solid product. In FIG. 7, curves 9 and 10 respectively represent the storage modulus and loss modulus of the composition of Example 2, and curves 11 and 12 respectively represent the storage modulus and loss modulus of the commercial product. As is clearly seen in FIG. 7, both the storage modulus and loss modulus of compositions according to the present invention are greater than that of the commercial product.

Figure 8:
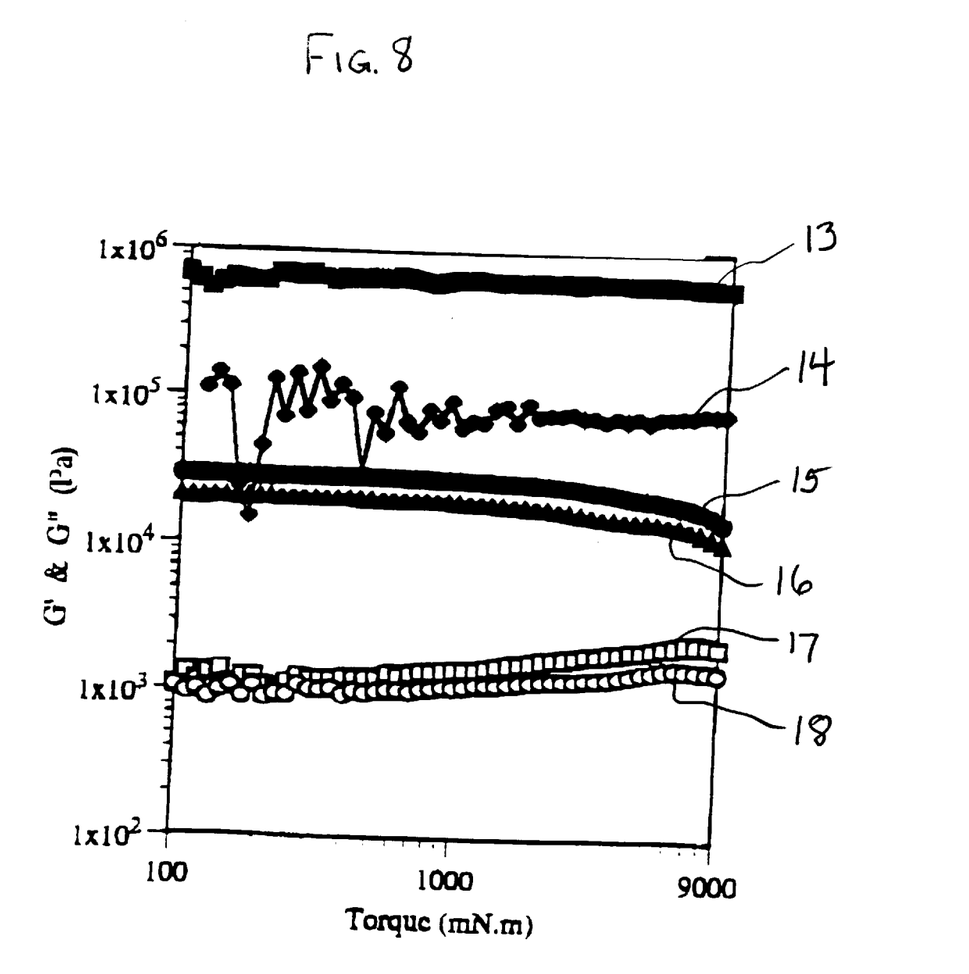
FIG. 8 is a graph showing both the storage modulus (elasticity) and loss modulus (viscosity) versus torque, for both a third embodiment of the present invention and commercial soft solid products.
Figure 9:
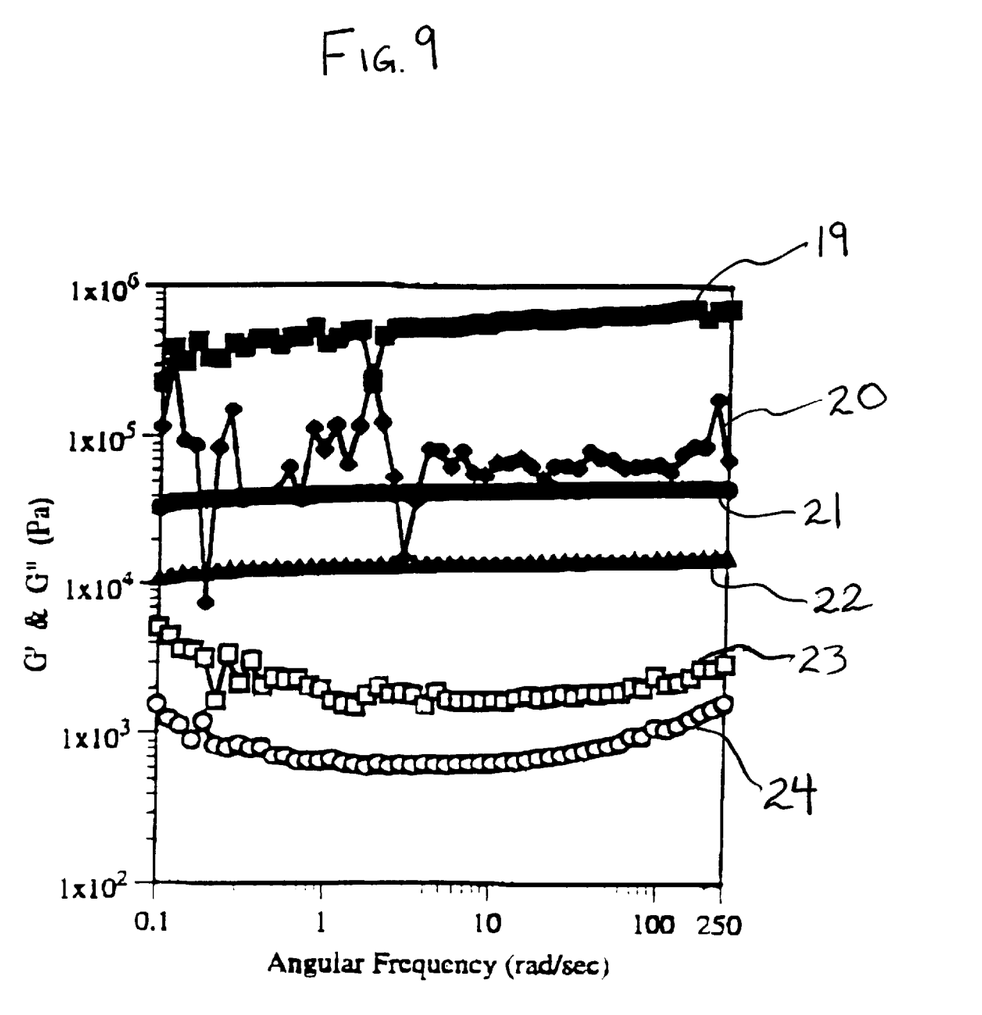
FIG. 9 is a graph showing both the storage modulus (elasticity) and loss modulus (viscosity) versus angular frequency, for both the third embodiment of the present invention and commercial soft solid products.

FIGS. 8 and 9 show the results of rheology measurements for the composition of Example 3 and for two commercial soft solid antiperspirant compositions. FIG. 8 shows the torque sweep, and FIG. 9 shows the frequency sweep. The results are similar to those achieved in connection with Examples 1 and 2. In FIG. 8, curves 13 and 14 respectively are the storage modulus and the loss modulus of the composition of Example 3; curves 15 and 16 respectively are the storage modulus and the loss modulus of a first commercial soft solid product; and curves 17 and 18 are the storage modulus and loss modulus of a second commercial soft solid product. In FIG. 9, curves 19 and 20 respectively are the storage modulus and the loss modulus of the composition of Example 3; curves 21 and 22 respectively are the storage modulus and the loss modulus of the first commercial product; and curves 23 and 24 respectively are the storage modulus and the loss modulus of the second commercial product. Neither the first nor the second commercial product contain, inter alia, the siliconyl beeswax as in Examples 1–3.

Figure 10:
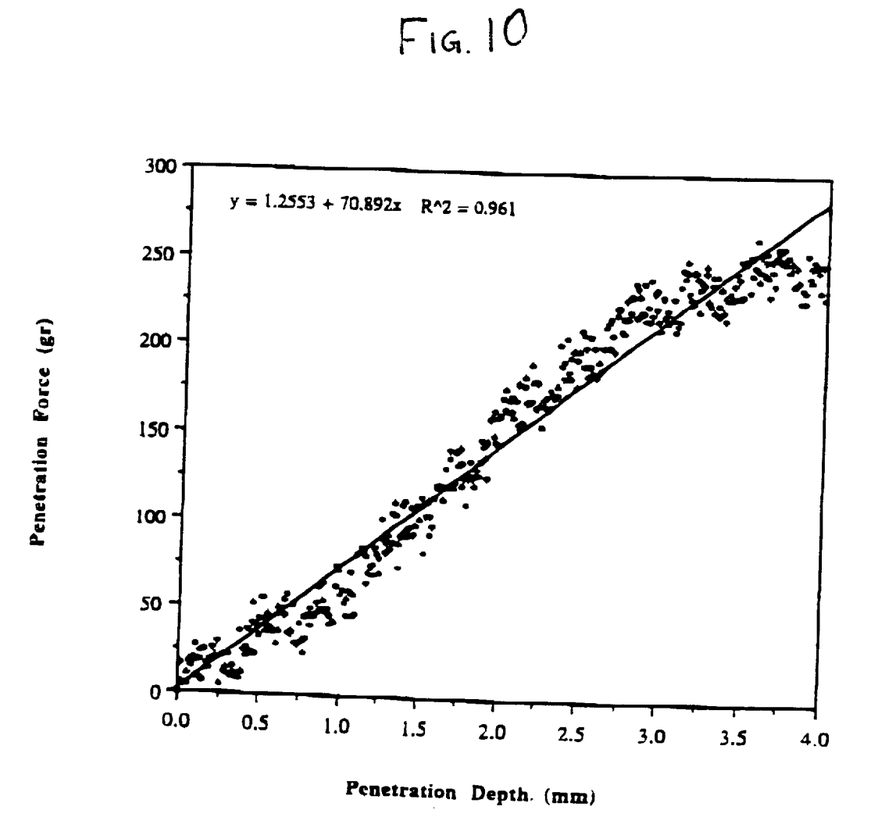
FIG. 10 is a graph of penetration force versus penetration depth for the third embodiment of the present invention.

FIG. 10 is a graph of penetration force versus penetration depth for the composition of Example 3, showing a substantially linear relationship therebetween.

Accordingly, by the present invention a non-aqueous, homogeneous composition can be provided for combatting body malodor, which is stable (e.g., does not exhibit any syneresis), and which does not leave any visible (white) residue either upon application or after drying of the applied composition. The composition has good rheological properties when formulated as a cream and has good cosmetic properties (including maintaining a soft skin feel). Moreover, the composition is easy to manufacture.

The subject matter of this application is related to the subject matter described in the application entitled "Solid Cosmetic Composition Containing Hexanediol-Behenyl Beeswax as Gelling Agent", naming Wilson Lee and Robert Bianchini as inventors (attorney docket no.: 851.34669X00), filed concurrently herewith, the contents of which are incorporated herein by reference in their entirety now accorded U.S. Ser. No. 08/709,443 and filed on Sep. 9, 1996.

While we have shown and described several embodiments in accordance with the present invention, it is understood that the same is not limited thereto, but is susceptible to numerous changes and modifications as known to one having ordinary skill in the art, and we therefore do not wish to be limited to the detail shown and described herein, but intend to cover all such modifications as are encompassed by the scope of the appended claims.

What is claimed is:

1. A non-aqueous composition, comprising (a) an antiperspirant active material;
   (b) a thickening agent comprising a gelling agent which is a solid plasticizer selected from the group consisting of hydroxypolyester, polydimethylsiloxanyl beeswax and mixtures thereof, the thickening agent being included in the composition in an amount sufficient to provide a solid composition;
   (c) volatile silicone material; and
   (d) non-volatile emollient material.

2. A non-aqueous composition, comprising in percent by weight based on the total weight of the composition:
   (a) an antiperspirant active material in an amount up to 30% by weight;
   (b) 5–20% by weight of a thickening agent comprising a gelling agent which is a solid plasticizer selected from the group consisting of hydroxypolyester, polydimethylsiloxanyl beeswax and mixtures thereof;
   (c) 30–70% by weight of a volatile silicone; and
   (d) 2–15% by weight of a non-volatile emollient material.

3. The composition according to claim 2, wherein the gelling agent is polydimethylsiloxanyl beeswax.

4. The composition according to claim 3, wherein the thickening agent is included in the composition in an amount sufficient to provide a cream composition.

5. The composition according to claim 4, wherein the antiperspirant active material is included in the composition in an amount sufficient to reduce flow of perspiration from the body.

6. The composition according to claim 5, wherein the antiperspirant active material is an antiperspirant active metal salt.

7. The composition according to claim 6, wherein the antiperspirant active metal salt is in particulate form suspended in the composition.

8. The composition according to claim 5, wherein the antiperspirant active material is in particulate form, suspended in the composition.

9. The composition according to claim 8, wherein the volatile silicone material is cyclomethicone.

10. The composition according to claim 8, wherein the non-volatile emollient material includes a non-volatile silicone emollient material.

11. The composition according to claim 10, wherein the non-volatile silicone emollient material is dimethicone.

12. The composition according to claim 8, wherein the non-volatile emollient material is PPG-14 butyl ether.

13. The composition according to claim 3, further comprising trihydroxystearin.

14. The composition according to claim 13, wherein the thickening agent is included in the composition in an amount sufficient to provide a cream composition.

15. The composition according to claim 14, wherein the antiperspirant active material is included in the composition in an amount sufficient to reduce flow of perspiration from the body.

16. The composition according to claim 15, wherein the antiperspirant active material is in particulate form, suspended in the composition.

17. The composition according to claim 1, further comprising trihydroxystearin.

18. The composition according to claim 17, wherein the antiperspirant active material is included in the composition in an amount sufficient to reduce flow of perspiration from the body.

19. The composition according to claim 18, wherein the antiperspirant active material is in particulate form suspended in the composition.

20. The composition according to claim 19, wherein the thickening agent is included in the composition in an amount sufficient to provide a cream composition.

21. The composition according to claim 1, wherein the antiperspirant active material is included in the composition in an amount sufficient to reduce flow of perspiration from the body.

22. The composition according to claim 21, wherein the antiperspirant active material is in particulate form suspended in the composition.

23. The composition according to claim 22, wherein the thickening agent is included in the composition in a amount sufficient to provide a cream composition.

24. The composition according to claim 1, wherein the gelling agent is a derivative of beeswax in which free fatty acids of the beeswax have been reacted with silicone materials.

25. The composition according to claim 1, wherein the gelling agent which is a solid plasticizer has a branched structure.

26. The composition according to claim 1, wherein the gelling agent is a hydroxy polyester.

27. The composition according to claim 26, wherein the hydroxy polyester is $C_{18-38}$ hydroxy stearate.

28. The composition according to claim 1, wherein the antiperspirant active material is included in the composition in an amount sufficient to have an antimicrobial effect but not sufficient to have an antiperspirant effect, whereby the composition is a deodorant composition.

29. A non-aqueous composition, comprising:
(a) 0.1–30% by weight, of the total weight of the composition, of an antiperspirant active material;
(b) a thickening agent, in an amount sufficient to provide a solid composition, the thickening agent including 5–20% by weight, of the total weight of the composition, of a gelling agent which is a solid plasticizer;
(c) 30–70% by weight, of the total weight of the composition, of volatile silicone material; and
(d) 2–15% by weight, of the total weight of the composition, of non-volatile emollient material.

30. The composition according to claim 29, further comprising 5–10% by weight, of the total weight of the composition, of trihydroxystearin.

31. The composition according to claim 29, wherein the non-volatile emollient material includes a non-volatile silicone emollient material.

32. The composition according to claim 31, wherein the non-volatile silicone emollient material is dimethicone.

33. The composition according to claim 29, wherein the non-volatile emollient material includes PPG-14 butyl ether.

34. The composition according to claim 29, wherein the composition includes 0.1–10% by weight, of the total weight of the composition, of antiperspirant active material.

35. The composition according to claim 29, wherein the composition includes 12–30% by weight, of the total weight of the composition, of antiperspirant active material.

36. The composition according to claim 29, wherein said gelling agent is at least one material selected from the group consisting of a hydroxy polyester and polydimethylsiloxanyl beeswax.

37. A method of reducing body malodor, comprising the step of applying the composition of claim 29 to axillary regions of the human.

38. A method of reducing body malodor, comprising the step of applying the composition of claim 21 to axillary regions of the human.

39. A method of reducing body malodor, comprising the step of applying the composition of claim 13 to axillary regions of the human.

40. A method of reducing body malodor, comprising the step of applying the composition of claim 5 to axillary regions of the human.

41. A method of reducing body malodor, comprising the step of applying the composition of claim 1 to axillary regions of the human.

* * * * *